(12) United States Patent
Archer et al.

(10) Patent No.: US 11,813,035 B2
(45) Date of Patent: *Nov. 14, 2023

(54) USE OF A PROGRESSIVE COMPRESSION ENCODING OF PHYSIOLOGIC WAVEFORM DATA IN AN IMPLANTABLE DEVICE TO SUPPORT DISCONTINUING TRANSMISSION OF LOW-VALUE DATA

(71) Applicant: NeuroPace, Inc., Mountain View, CA (US)

(72) Inventors: Stephen T. Archer, Sunnyvale, CA (US); Patrick Gerard Mulligan, Belmont, CA (US); David A. Greene, Fort Wayne, IN (US)

(73) Assignee: NeuroPace, Inc., Mountain View, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 17/521,652

(22) Filed: Nov. 8, 2021

(65) Prior Publication Data

US 2022/0061663 A1 Mar. 3, 2022

Related U.S. Application Data

(60) Continuation of application No. 16/256,966, filed on Jan. 24, 2019, now Pat. No. 11,206,979, which is a division of application No. 14/270,212, filed on May 5, 2014, now Pat. No. 10,231,621.

(51) Int. Cl.
*A61B 5/00* (2006.01)
*A61B 5/24* (2021.01)
*G16H 40/63* (2018.01)
*G16H 10/60* (2018.01)
*G16H 10/65* (2018.01)
*A61B 5/316* (2021.01)
*A61B 5/369* (2021.01)

(52) U.S. Cl.
CPC .............. *A61B 5/00* (2013.01); *A61B 5/0002* (2013.01); *A61B 5/0031* (2013.01); *A61B 5/24* (2021.01); *A61B 5/316* (2021.01); *A61B 5/4094* (2013.01); *A61B 5/7282* (2013.01); *G16H 10/60* (2018.01); *G16H 10/65* (2018.01); *G16H 40/63* (2018.01); *A61B 5/369* (2021.01); *A61B 2560/0209* (2013.01)

(58) Field of Classification Search
None
See application file for complete search history.

(56) References Cited

U.S. PATENT DOCUMENTS

| 6,016,449 A | 1/2000 | Fischell et al. |
| 2006/0094968 A1 | 5/2006 | Drew |
| 2007/0098379 A1 | 5/2007 | Wang et al. |

(Continued)

*Primary Examiner* — Etsub D Berhanu
(74) *Attorney, Agent, or Firm* — LOZA & LOZA, LLP; David S. Sarisky

(57) ABSTRACT

An external data retrieval apparatus receives a low resolution version of a physiological signal from an active implantable medical device and determines if the physiological signal represents a clinically significant event. The apparatus provides an indication of such determination to the implantable medical device. If the physiological signal does represent a clinically significant event, the apparatus receives a full download of the physiological signal from the implantable device.

18 Claims, 11 Drawing Sheets

(56) References Cited

U.S. PATENT DOCUMENTS

| | | |
|---|---|---|
| 2007/0110305 A1 | 5/2007 | Corcoran et al. |
| 2007/0150024 A1 | 6/2007 | Leyde et al. |
| 2007/0192408 A1 | 8/2007 | Konig |
| 2007/0249953 A1 | 10/2007 | Frei et al. |
| 2008/0139881 A1 | 6/2008 | Cover et al. |
| 2010/0121215 A1 | 5/2010 | Giftakis et al. |
| 2010/0217147 A1 | 8/2010 | Odame |
| 2011/0137132 A1 | 6/2011 | Gustafson |
| 2011/0190595 A1 | 8/2011 | Bennett et al. |
| 2012/0262303 A1* | 10/2012 | Fahey ............... A61B 5/14552 |
| | | 340/870.02 |
| 2013/0096391 A1 | 4/2013 | Osorio et al. |

* cited by examiner

| Absolute Difference | Number of Samples | Percent |
|---|---|---|
| 0-1 | 3689 | 16.41% |
| 2-5 | 8757 | 38.95% |
| 6-10 | 6211 | 27.63% |
| 11-20 | 3244 | 14.43% |
| 21-50 | 539 | 2.40% |
| 51-99 | 36 | 0.16% |
| 100-255 | 5 | 0.02% |

USE OF A PROGRESSIVE COMPRESSION ENCODING OF PHYSIOLOGIC WAVEFORM DATA IN AN IMPLANTABLE DEVICE TO SUPPORT DISCONTINUING TRANSMISSION OF LOW-VALUE DATA

CROSS-REFERENCE TO RELATED APPLICATIONS

This application is a continuation application of U.S. patent application Ser. No. 16/256,966, filed Jan. 24, 2019, now U.S. Pat. No. 11,206,979 for "Use of a Progressive Compression Encoding of Physiologic Waveform Data in an Implantable Device to Support Discontinuing Transmission of Low-Value Data," which is a divisional application of U.S. patent application Ser. No. 14/270,212, filed May 5, 2014, now U.S. Pat. No. 10,231,621 for "Use of a Progressive Compression Encoding of Physiologic Waveform Data in an Implantable Device to Support Discontinuing Transmission of Low-Value Data."

TECHNICAL FIELD

The present disclosure relates generally to transmission of data by active implantable medical devices, and more particularly, to apparatuses and methods for optimizing the transmission of data from active implantable medical devices.

BACKGROUND

Modern active implantable medical devices, such as neurostimulators, pacemakers, and ICDs, are capable of not only monitoring patient condition and delivering therapy, but are capable of storing detailed data and diagnostics relating to a patient's condition for later retrieval. Analysis of this data can improve patient care dramatically, and allow fine-tuning the performance of the implantable devices by programming them with new operational parameters. Interrogation of an implantable medical device allows data stored in the device to be retrieved by an external device. After analysis, reprogramming the device allows its performance to be optimized based on the interrogated data.

Often it is desirable to store large quantities of data in the implantable device until such time as the data can be transmitted from the implantable device to external equipment such as a physician programmer or a home data monitor. Once the physiologic data has been retrieved by the external equipment it is often incorporated into data repository and made available for display and analysis. The resources available in an implantable device are often very limited. For example, the memory resources aboard an implantable device are limited by the small physical size constraints imposed on the design. Only physically small and low power memory media are practical for this use. Typically, this limits the design to relatively small storage capacity CMOS static RAM or similar devices.

The power source for implantable devices is often a small primary cell (non-rechargeable battery). The usable service life of an implantable device is typically determined by how quickly the battery is depleted. When the battery is depleted the usable service life is over. Minimizing the duration of high power activities such as telemetry reduces the rate of battery depletion and so increases useful service life.

Implantable medical device systems often include a home data monitor. This provides the opportunity to upload physiologic data conveniently and often. This reduces the demand for memory space onboard the implantable device by affording opportunities to retrieve the contents of this memory often. However, the home data monitor also increases the demand for transporting large quantities of data over telemetry to external equipment. This increased telemetry activity increases the rate of battery depletion thereby reducing the useable service life for the implantable device.

It would be desirable to provide mechanisms that optimize the retrieval of patient data in a manner that reduces implantable medical device energy consumption and conserves memory space. The concepts disclosed below address these needs and others.

SUMMARY

In one implementation, an external data retrieval apparatus receives a low resolution version of a physiological signal from an active implantable medical device and determines if the physiological signal represents a clinically significant event. The apparatus provides an indication of such determination to the implantable medical device. If the physiological signal does represent a clinically significant event, the apparatus receives a full download of the physiological signal from the implantable device.

In another implementation, an implantable medical device obtains data representative of a physiological signal sensed by the implantable medical device, and transmits data corresponding to a low resolution version of the physiological signal to an external data retrieval device. The device subsequently receives an indication from the external data retrieval device as to whether the physiological signal represents a clinically significant event; and transmits data corresponding to a high resolution version of the physiological signal when the signal represents a clinically significant event.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of apparatuses and methods will now be presented in the detailed description by way of example, and not by way of limitation, with reference to the accompanying drawings, wherein.

DETAILED DESCRIPTION

Figure 1:
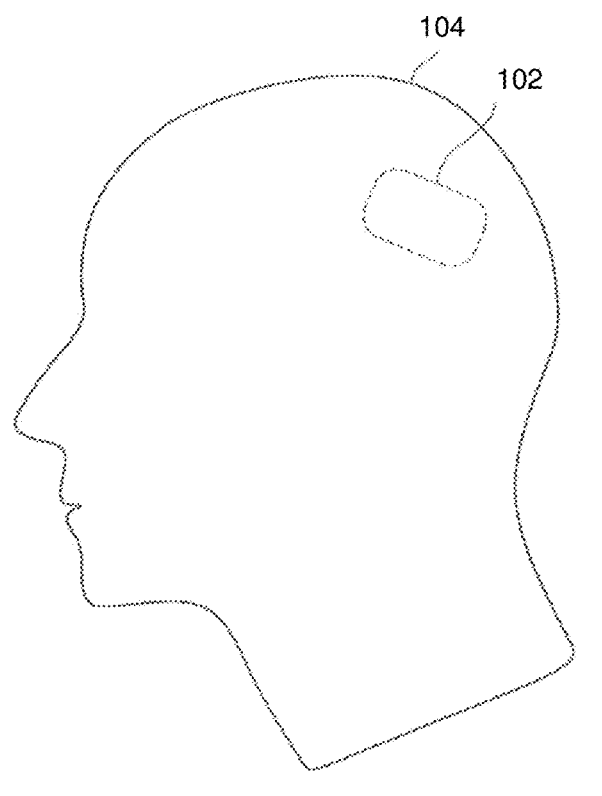
FIG. 1 is a schematic illustration of a patient's head showing the placement of an implantable medical device.

Various aspects of the disclosure will be described more fully hereinafter with reference to the accompanying drawings. This disclosure may, however, be embodied in many different forms by those skilled in the art and should not be construed as limited to any specific structure or function presented herein. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of this disclosure, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure and/or functionality in addition to or instead of other aspects of this disclosure. It should be understood that any aspect of the disclosure disclosed herein may be embodied by one or more elements of a claim.

The concepts disclosed may be implemented in hardware or software that is executed on a hardware platform. The hardware or hardware platform may be a general purpose processor, a digital signal processor (DSP), an application specific integrated circuit (ASIC), a field programmable gate array (FPGA) or other programmable logic component, discrete gate or transistor logic, discrete hardware components, or any combination thereof, or any other suitable component designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a plurality of microprocessors, one or more microprocessors in conjunction with a DSP, or any other such configuration.

Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on a computer-readable medium. A computer-readable medium may include, by way of example, a magnetic storage device (e.g., hard disk, floppy disk, magnetic strip), an optical disk (e.g., compact disk (CD), digital versatile disk (DVD)), a smart card, a flash memory device (e.g., card, stick, key drive), random access memory (RAM), read only memory (ROM), programmable ROM (PROM), erasable PROM (EPROM), electrically erasable PROM (EEPROM), a general register, or any other suitable non-transitory medium for storing software.

As mention above, an implantable medical device (IMD) such as a pacemaker, implantable defibrillator, or neurostimulator stores data that are useful for assessing patient medical status and for determining the operational status of the implantable medical device. However, the amount of memory present in the implantable medical device is limited, so eventually the implantable medical device may stop storing data, or may need to overwrite older data to store new data. The term "overwrite" is used herein to describe data loss resulting from limited memory. To avoid overwrite, it is desirable to have a home appliance that can retrieve data from the implantable medical device between office visits in the patient's home. Such a home appliance, hereafter referred to as a data retrieval apparatus (DRA), would ideally use radio frequency (RF) telemetry to retrieve data transcutaneously from the implantable medical device when the patient is in close proximity. The data retrieval apparatus could be a standalone device that the patient would bring to their physician for read-out, or it could be internet connected to a central database. Ideally the data retrieval apparatus would have a telemetry range long enough for it to be placed in a convenient location where it could establish the telemetry link on a periodic basis without patient intervention. The methods and apparatuses described herein (1) automate the setup process of the data retrieval apparatus for both the patient and physician, (2) avoid data overwrite, and (3) minimize the energy consumed by the implantable medical device when transmitting data to the data retrieval apparatus. Automation of the setup process reduces physician workload. Avoiding data overwrite improves patient assessment and care. Reducing energy consumed by the implantable medical device during data transmission increases the life of the implantable medical device's battery and reduces the frequency of implantable medical device replacement surgical procedures, which in turn lowers surgical complications and reduces total medical costs.

With reference to FIG. 1, an exemplary implantable medical device 102 is shown implanted in a patient 104. In one configuration, the implantable medical device 102 includes a small self-contained brainwave detecting device. As the term is used herein, a brainwave detecting or recording device is a device capable of detecting or predicting ictal activity (or other neurological events) for providing data useful in the diagnosis of a neurological disorder. Further, the term recording device, as used herein, is a device that can either record neurological signals, such as EEG signals, or detect and analyze EEG signals and create a log of such an analysis.

The implantable medical device 102 may be configured to detect or predict neurological events that have a representative electrographic signature. For example, the implantable medical device 102 may be responsive to epileptic seizures. It should, however, be recognized that it is also possible to respond to other types of neurological disorders, such as movement disorders (e.g. the tremors characterizing Parkinson's disease), migraine headaches, chronic pain, and neuropsychiatric disorders such as depression.

Figure 2:
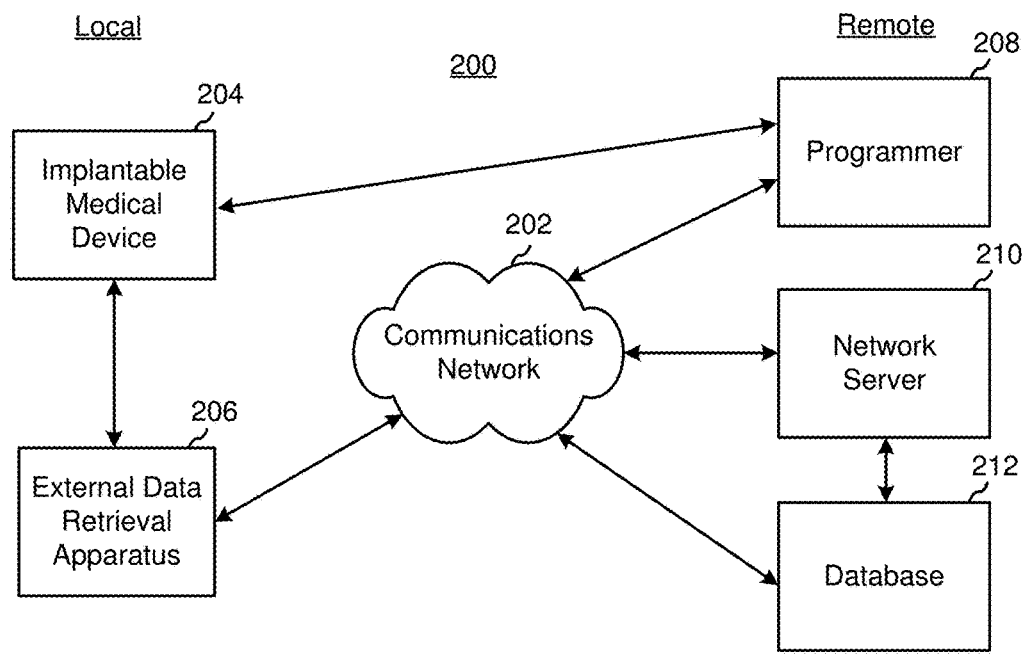
FIG. 2 is a block diagram of a system for providing communication between local medical devices and remote system components.

With reference to FIG. 2, an exemplary patient monitoring system 200 is illustrated. The patient monitoring system 200 includes local components and remote components that communicate through a communications network 202, such as the Internet. Local components are located in the vicinity of the patient, such as the patient's residence, and may include an implantable medical device 204, and a local device 206, referred to herein as a data retrieval apparatus. Remote components are located a significant distance from the patient, such as at a hospital or care provider's office. Remote components may include, for example, a programmer 208, a network server 210 and a database 212.

The programmer 208 is typically operated by medical personnel (such as the patient's treating physician) to control the operation of the implantable medical device 204. In general terms, the programmer 208 functions as a clinical interface to the implantable medical device 204, allowing the implantable medical device parameters to be modified, and for data and/or program code to be uploaded from and downloaded to the implantable medical device.

The database 212 serves as a centralized data repository for all data relevant to the operation of the system 200, and may include clinical data, program code, and more. The network server 210 acts as the primary interface between the database 212 and other devices attached to the communications network 202. Although it might be possible and advantageous in certain circumstances to communicate directly with the database 212, it is generally preferable to configure the network server 210 to receive queries, perform necessary authentication, access the database 212, and respond as necessary, thereby reducing the processing load on the database and also reducing the exposure of the database to network traffic (thereby improving security).

The data retrieval apparatus 206 is configured to receive data from remote components through the communications network 202 and provide it to the implantable medical device 204. Such data may include, for example, program code or instructions from a programmer 208 that affect the operation of the implantable medical device 204. The data retrieval apparatus 206 is also configured to retrieve data from the implantable medical device 204 and to forward it to one or more of the remote components. As described further below, communication between the data retrieval apparatus 202 and the implantable medical device 204 is wireless, and may be in the form of short-range telemetry by inductive coupling or long-range telemetry by RF communications.

Figure 3:
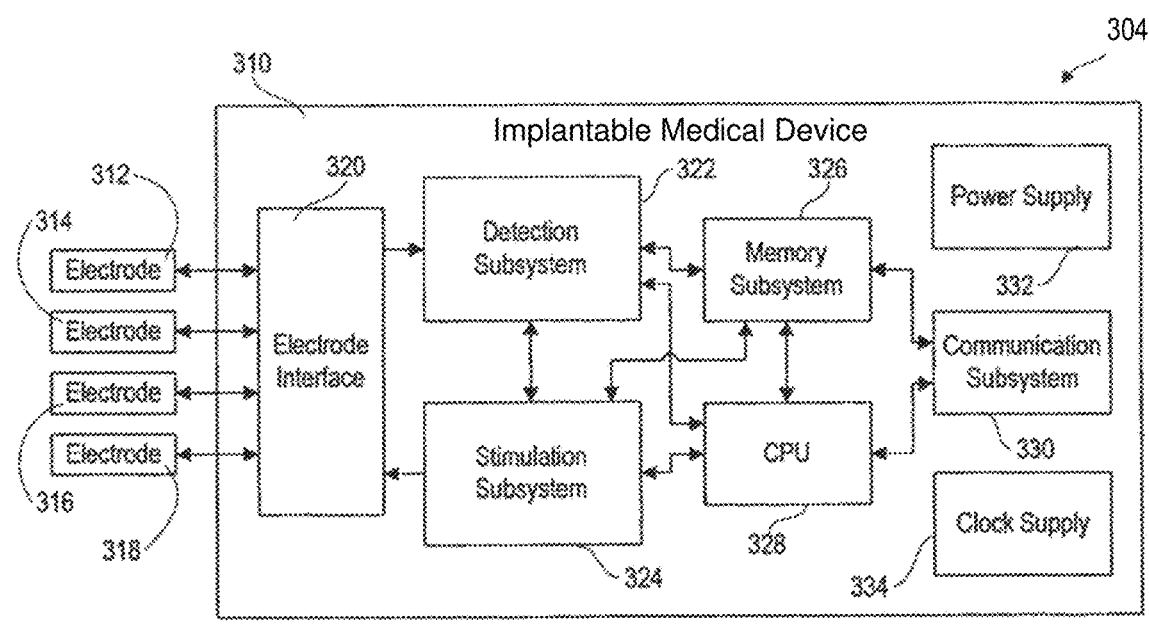
FIG. 3 is a block diagram of an implantable medical device.

An overall block diagram of an implantable medical device 304 used for measurement, detection, and treatment is illustrated in FIG. 3. Inside the housing of the device 304 are several subsystems making up a control module 310. The control module 310 is capable of being coupled to a plurality of electrodes 312, 314, 316, and 318 for sensing and stimulation. Although four electrodes are shown in FIG. 3, it should be recognized that any number is possible.

The electrodes 312-318 are connected to an electrode interface 320. Preferably, the electrode interface is capable of selecting each electrode as required for sensing and stimulation; accordingly the electrode interface is coupled to a detection subsystem 322 and a stimulation subsystem 324. The electrode interface also may provide any other features, capabilities, or aspects, including but not limited to amplification, isolation, and charge-balancing functions, that are required for a proper interface with neurological tissue and not provided by any other subsystem of the implantable medical device 304.

The detection subsystem 322 includes an EEG analyzer function. The EEG analyzer function is adapted to receive EEG signals from the electrodes 312-318, through the electrode interface 320, and to process those EEG signals to identify neurological activity indicative of a seizure, an onset of a seizure, or a precursor to a seizure. One way to implement such EEG analysis functionality is disclosed in detail in U.S. Pat. No. 6,016,449 to Fischell et al., which is hereby incorporated by reference. The detection subsystem may optionally also contain further sensing and detection capabilities, including but not limited to parameters derived from other physiological conditions (such as electrophysiological parameters, temperature, blood pressure, etc.).

The stimulation subsystem 324 is capable of applying electrical stimulation to neurological tissue through the electrodes 312-318. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal events detected by the EEG analyzer function of the detection subsystem 322. As illustrated in FIG. 3, the stimulation subsystem 324 and the EEG analyzer function of the detection subsystem 322 are in communication; this facilitates the ability of stimulation subsystem 324 to provide responsive stimulation as well as an ability of the detection subsystem 322 to blank the amplifiers while stimulation is being performed to minimize stimulation artifacts. It is contemplated that the parameters of the stimulation signal (e.g., frequency, duration, waveform) provided by the stimulation subsystem 324 would be specified by other subsystems in the control module 310.

Also in the control module 310 is a memory subsystem 326 and a central processing unit (CPU) 328, which can take the form of a microcontroller. The memory subsystem 326 is coupled to the detection subsystem 322 (e.g., for receiving and storing data representative of sensed EEG signals and evoked responses), the stimulation subsystem 324 (e.g., for providing stimulation waveform parameters to the stimulation subsystem), and the CPU 328, which can control the operation of the memory subsystem 326. In addition to the memory subsystem 326, the CPU 328 is also connected to the detection subsystem 322 and the stimulation subsystem 324 for direct control of those subsystems. A compression module (not shown) may be located between the detection subsystem 322 and the memory subsystem 326. The compression module is configured to compress data, e.g., ECOG data, sensed by the detection subsystem 322 prior to storage in the memory subsystem 326.

The memory subsystem 326 may include one or more types of memory, including for example, random access memory (RAM), read only memory (ROM), and non-volatile memory (NVM). As explained further below, within one or more of the types of memory, such as RAM, there may be sections of memory reserved for the following: 1) EEG waveform data (stored ECOG's), 2) detailed event data regarding detection activity, 3) long-term histogram data on detections, and 4) device diagnostic information (battery voltage, lead impedance, radio usage, etc)

Also provided in the control module 310, and coupled to the memory subsystem 326 and the CPU 328, is a communication subsystem 330. The communication subsystem 330 enables communication between the implantable medical device 204 (FIG. 2) and the outside world, e.g., the data retrieval apparatus 206 (FIG. 2). The communication subsystem 330 may include a telemetry coil (which may be situated outside of the housing) enabling short-range transmission and reception of signals, to or from the implantable medical device 204, via inductive coupling. The communication subsystem 330 may also include a transceiver and one or more antennas for long-range telemetry by an RF communications link with the implantable medical device 204.

Rounding out the subsystems in the control module 310 are a power supply 332 and a clock supply 334. The power supply 332 supplies the voltages and currents necessary for each of the other subsystems. The clock supply 334 supplies substantially all of the other subsystems with any clock and timing signals necessary for their operation.

While the memory subsystem 326 is illustrated in FIG. 3 as a separate functional subsystem, the other subsystems may also require various amounts of memory to perform the functions described above and others. Furthermore, while the control module 310 is preferably a single physical unit contained within a single physical enclosure, namely the housing, it may comprise a plurality of spatially separate units each performing a subset of the capabilities described above. Also, the various functions and capabilities of the subsystems described above may be performed by electronic hardware, computer software (or firmware), or a combination thereof.

Figure 4:
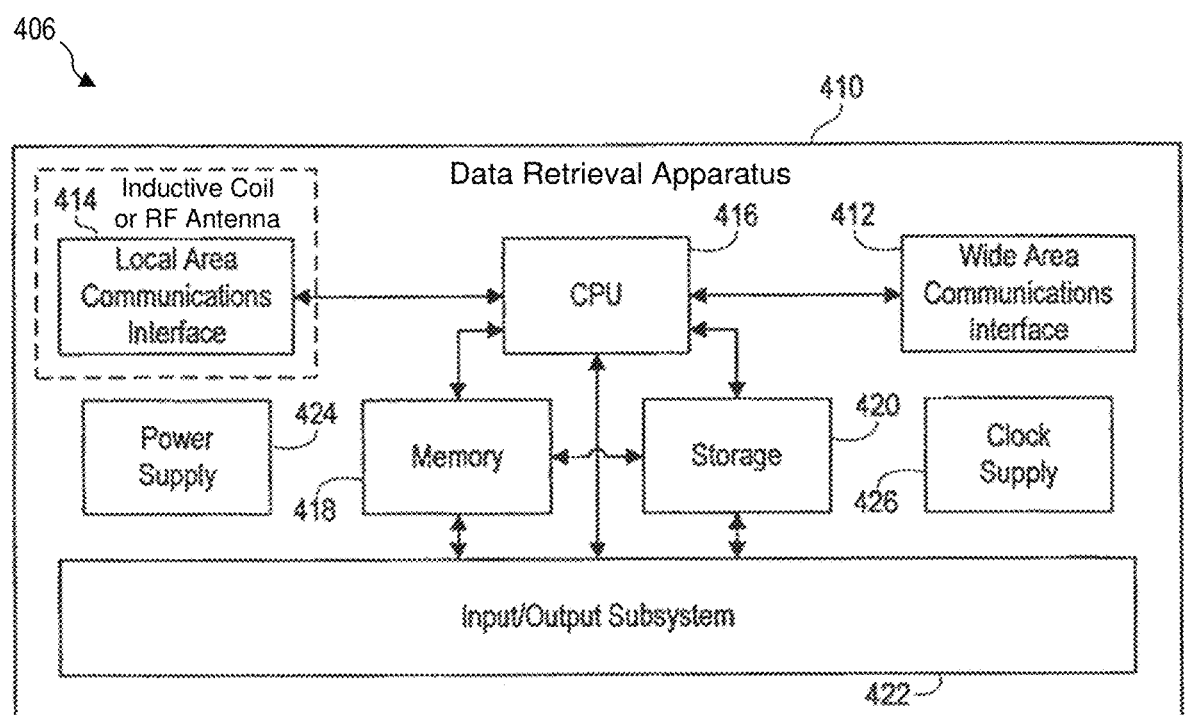
FIG. 4 is a block diagram of a data retrieval apparatus.

Referring now to FIG. 4, a block diagram representing a data retrieval apparatus 406 is set forth in detail. The data retrieval apparatus 406 includes a general-purpose or special-purpose computer programmed or adapted for use as described herein. The data retrieval apparatus 406 includes a wide area communications interface 412 for communications with the communications network 202 (FIG. 2), and a local area communications interface 414 for communications with the implantable medical device 204. The wide area communications interface 412 may be, for example, an Internet connection. The local area communications interface 414 may be an inductive short-range telemetry system including an inductive coil, or a long-range RF telemetry system including an RF antenna. The method and apparatuses disclosed herein are primarily directed to RF telemetry communications. Preferably, both the wide area communications interface 412 and the local area communications interface 414 are capable of bi-directional communications.

The data retrieval apparatus 406 is controlled by a CPU 416. The CPU is coupled, either directly or through a bus controller, to the wide area communications interface 412, the local area communications interface 414, a memory subsystem 418 for programming and short-term storage, a storage subsystem 420 (which might include a hard drive, flash memory, and other non-volatile storage), and an input/output subsystem 422 used to pass information to and receive information from a user. The memory subsystem 418 may include ROM, dynamic RAM, and other random-access memory. The storage subsystem 420 may include a hard drive, flash memory, and other non-volatile storage.

The operation of the data retrieval apparatus 406 is controlled by a power supply 424 and a clock supply 426. The power supply 424 typically includes batteries. Alternatively, the data retrieval apparatus 406 may receive power from an AC outlet. A combination of the two sources might also be used. The clock supply 426 supplies substantially all of the other subsystems of the network unit with any clock and timing signals necessary for their operation.

As with the implantable medical device 304 (FIG. 3) described above, while the memory subsystem 418 is illustrated in FIG. 4 as a separate functional subsystem, the other subsystems may also require various amounts of memory to perform the functions described herein and others. Furthermore, while the data retrieval apparatus 406 is preferably a single physical unit contained within a single physical enclosure, namely the housing, it may comprise a plurality of spatially separate units each performing a subset of the capabilities described herein.

The various functions and capabilities of the subsystems of the data retrieval apparatus 406 described above may be performed by electronic hardware, computer software, or firmware, or a combination thereof. The illustration of FIG. 4 shows several of the major functional subsystems present in a data retrieval apparatus consistent with the invention. However, in many computing systems, other functional subsystems and modules are present that are not necessarily reflected in FIG. 4. Moreover, a data retrieval apparatus 406 may integrate two or more of the above-referenced subsystems. For example, the wide area communications interface 412 and the local area communications interface 414 might be adapted into a single subsystem if efficiencies result there from. Accordingly, FIG. 4 is for purposes of illustration only, and does not necessarily reflect the actual configuration of the data retrieval apparatus. It is, however, considered to be representative.

As noted above, active implantable medical devices that monitor and record physiologic signals can generate and store large quantities of data. Memory and power resources available in an implantable device, however, are often very limited. Regarding memory, such resources aboard an implantable device are limited by the small physical size constraints imposed on the design. Only physically small and low power memory media are practical for this use. Typically, this limits the design to relatively small storage capacity CMOS static RAM or similar devices. Regarding power, such resource for implantable devices is often a small primary cell (non-rechargeable battery). The usable service life of an implantable device is typically determined by how quickly the battery is depleted. When the battery is depleted the usable service life is over.

Implantable systems often include a home data monitor. The monitor provides the opportunity to upload physiologic data conveniently and often, and reduces the demand for memory space onboard the implantable device by affording opportunities to retrieve the contents of memory often. However, the home data monitor also increases the demand for transporting large quantities of data over telemetry to external equipment. This increased telemetry activity increases the rate of battery depletion thereby reducing the useable service life for the implantable device.

Disclosed herein are techniques that minimize the duration of high power activities, such as telemetry of physiologic data from the implanted device to the external equipment, to thereby reduce the rate of battery depletion and increase device longevity. The disclosed techniques also conserve memory space by providing compression of the physiologic data as it is being stored.

Well known progressive encoding systems (e.g., JPEG) are often used for storing large image files such as those from digital cameras. Progressive encoding allows an image to be displayed at low resolution after only a small portion of the image file has been retrieved for example over a slow data link. Thus, a low resolution version of the image can be displayed very quickly after only a small portion of data has been retrieved. As more data slowly streams in, the image can be displayed in higher and higher resolution until the download is complete.

In systems and methods disclosed herein, physiologic waveform (e.g., ECOG waveform) data recorded by an active implantable medical device is compressed by the device using a progressive encoding system, e.g., JPEG. During a telemetry session with an external apparatus, the implantable device transmits to the external apparatus, a portion of an encoded file representing a low resolution version of a physiologic waveform. Once uploaded to the external apparatus, the apparatus has a low resolution version of the waveform available for analysis. Algorithms within the external apparatus make a determination of the value of the waveform. If the waveform is deemed of interest, or valuable, the upload is allowed to complete until a full resolution version of the waveform is received. If the waveform is not deemed valuable, the upload is discontinued. Discontinuing the upload of waveforms that are not valuable reduces the duration of the telemetry activity which in turn reduces the rate of battery depletion and extends the usable implant service life.

A waveform could be deemed valuable if even in the low resolution version is determined to be novel or different from other waveforms collected from the same implantable device. High value may be assigned to waveforms that result directly from a patient action such as the application of the magnet to the implantable device, or to waveforms that fit other predetermined criteria. A waveform could be considered of low value if the low resolution version is determined to be similar to other waveforms already collected. Even though the uploading of the low value waveform is discontinued the low resolution version of the waveform may be stored in the central data repository along with diagnostic information explaining why the full resolution waveform was not retrieved from the implantable device.

Full download is desired for an ECOG that represents a clinically significant event. ECOG characteristics that can indicate clinically significant events include significant changes in signal amplitude and spectral content, both of which can result in ECOG power changes.

Total Power Change

Figure 5:
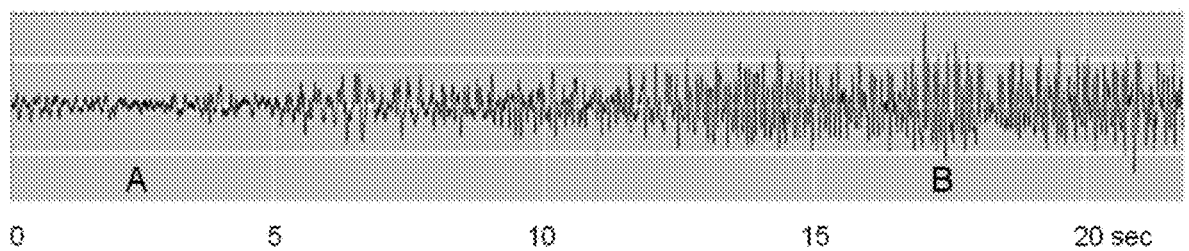
FIG. 5 is an illustration of an ECOG waveform of a developing seizure in an epileptic patient.

In one configuration, systems and methods determine if a low resolution ECOG represents a clinically significant event based on total power change in the ECOG signal when a seizure develops and spreads. FIG. 5 is an illustration of an ECOG waveform of a developing seizure in an epileptic patient. In FIG. 5, the power present in the signal increases significantly from point A to point B.

The y-axis of the ECOG signal is amplified voltage and is proportional to the intrinsic ECOG voltage at the output from a non-saturated linear amplifier. Instantaneous power is the product of the ECOG voltage and ECOG current. ECOG current is related to the ECOG voltage by the source impedance, which can be measured, but typically is not precisely known. However, the source impedance should be constant over the desired timeframes so ECOG power can be approximated by the square of the ECOG voltage.

Figure 6:
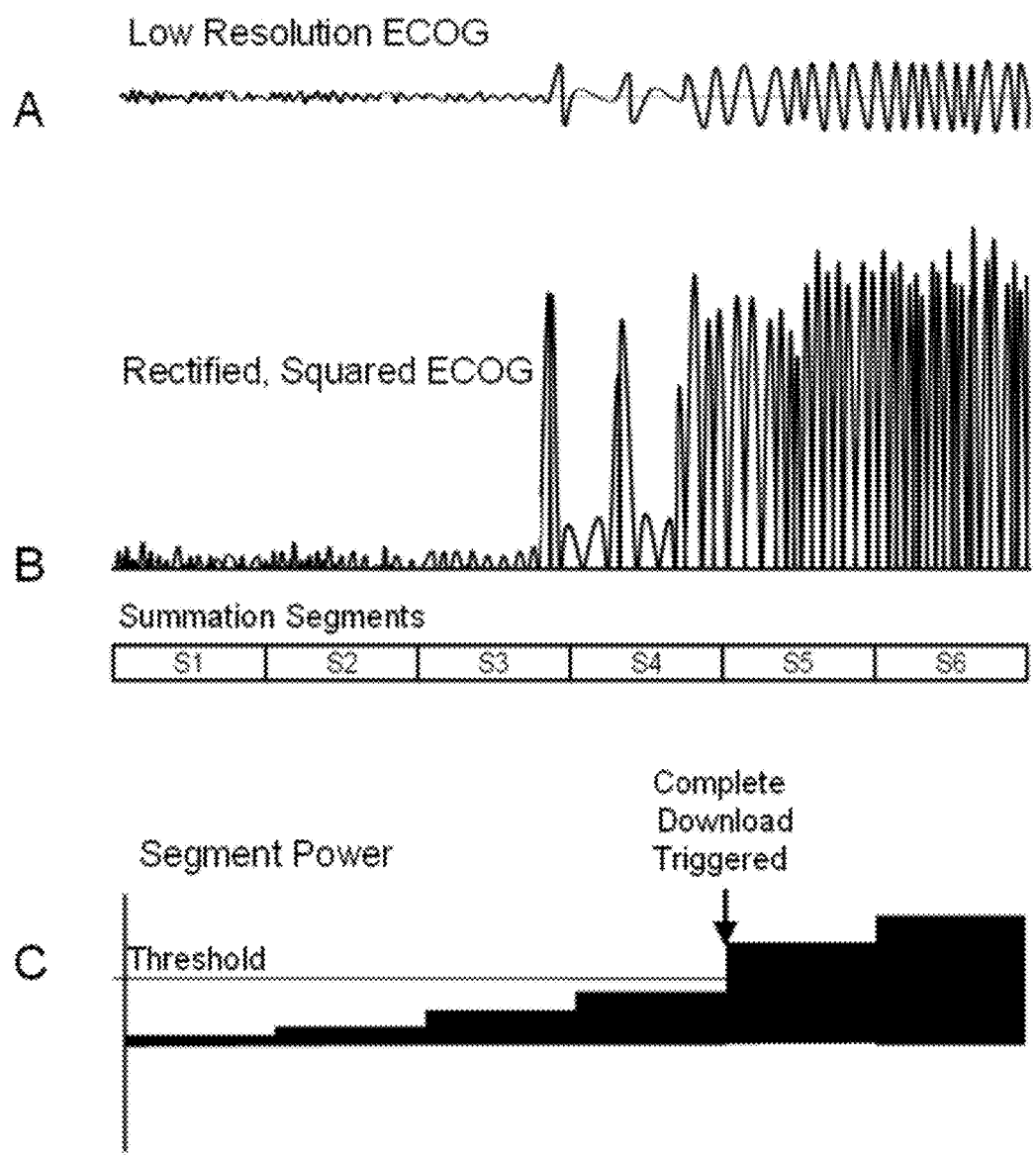
FIG. 6 includes illustrations of different stages of ECOG waveform analysis involved in the use of ECOG power to trigger full ECOG download.

FIG. 6 includes illustrations of different stages of ECOG waveform analysis involved in the use of ECOG power to determine if a low resolution ECOG waveform represents a clinically significant event so as to trigger full ECOG download. FIG. 6 illustrates an embodiment that uses ECOG power to trigger full ECOG download. In panel A the low resolution ECOG is shown. Using standard techniques known to those of ordinary skill in the art, the ECOG waveform is rectified and then squared to show a signal proportional to the ECOG power as shown in panel B. Using a series of summation registers labeled S1 to S6 in panel B, the power within time segments is determined for the time periods corresponding to the summation registers S1 thru S6. These register durations would typically be 1 to 30 seconds in duration. The summation registers may overlap in time in some embodiments to produce a smoothing effect if desired, but are shown without time overlap in FIG. 6. In the event the data are sampled at fixed intervals, the summed areas may be calculated by summing the sampled values, which produces computational efficiencies.

To determine if the low resolution waveform represents a clinically significant event so as to trigger a full ECOG download, the summation register values are compared to a criterion, such as a threshold. If one or more of the register values exceeds the threshold, the low resolution waveform is deemed to represent a clinically significant event, and full download of the waveform is triggered. In one configuration, the threshold may be based on the segment power exceeding a given level. In another configuration, the threshold may be based on the difference in the segment power between adjacent segments exceeding a given level. For example, if the difference between the segment power of segment S1 and segment S2 exceeds a difference threshold, then the low resolution waveform is deemed to represent a clinically significant event. Furthermore, although the segment power is shown as increasing in the example of FIG. 6, the threshold could be negative with power depletions being the triggering event.

The threshold for determining if a low resolution waveform represents a clinically significant event and triggering full ECOG download could be fixed or may be a percentage above a background trend. In one configuration, the running average of several summation registers at the beginning of each ECOG may be used as a baseline. Abrupt changes within each ECOG, relative to the baseline, would result in a determination if that low resolution waveform represents a clinically significant event, and trigger full ECOG download. Use of a running average is beneficial in that it allows for biocalibration of the threshold based on inherent background power levels which vary based on neural state (asleep, drowsy, awake, alert, etc). In this manner the threshold for an individual ECOG could be set as a multiple (100%, 200%, etc.) of the average segment power or segment power differences observed at the beginning of that ECOG.

In another configuration, the external apparatus may be configured to always fully retrieve a fixed number of ECOGs (1, 2, etc.). In this case, the external apparatus derives a power metric, e.g., segment power level or segment power difference, for each available low-resolution ECOG that is being considered for retrieval, and selects for full download, a number of low resolution ECOGs corresponding to the fixed number based on the respective metrics. For example, if the external apparatus is configured to retrieve 3 full resolution ECOGs per interrogation session, the ECOGs with the three highest segment powers or segment power differences are selected.

The power threshold could also be determined based on measured changes determined during prior ECOG retrieval sessions. For example, the external apparatus could have an evolving threshold that triggers full download for ECOGs that exhibit maximum segment power or maximum segment power difference that exceeds a certain percentage of observations for all prior sessions. In this embodiment, the external apparatus tracks all ECOG maximum segment power or maximum segment difference values over all retrieval sessions, and then sets the threshold to a percentage of the prior observations (80%, 90%, etc.). Metrics, e.g., maximum segment power or maximum segment power difference, are derived for new ECOGs and compared to the threshold. If the metric of the new ECOG exceeds the corresponding metric of the threshold percentage of the prior ECOGs, the new ECOG is determined to be a clinically significant event. For example, if the threshold percentage is 80% and the metric of the new ECOG is greater than the same metric of 80% of the prior ECOGs, the new ECOG is clinically significant, and a full download of the new ECOG is triggered. As new ECOGs are presented, the external apparatus adjusts the threshold. In this manner the ECOGs with the most powerful segments or segment differences would always be fully retrieved, which presumably would have the highest clinical significance.

Spectral Band Power Content

Figure 7:
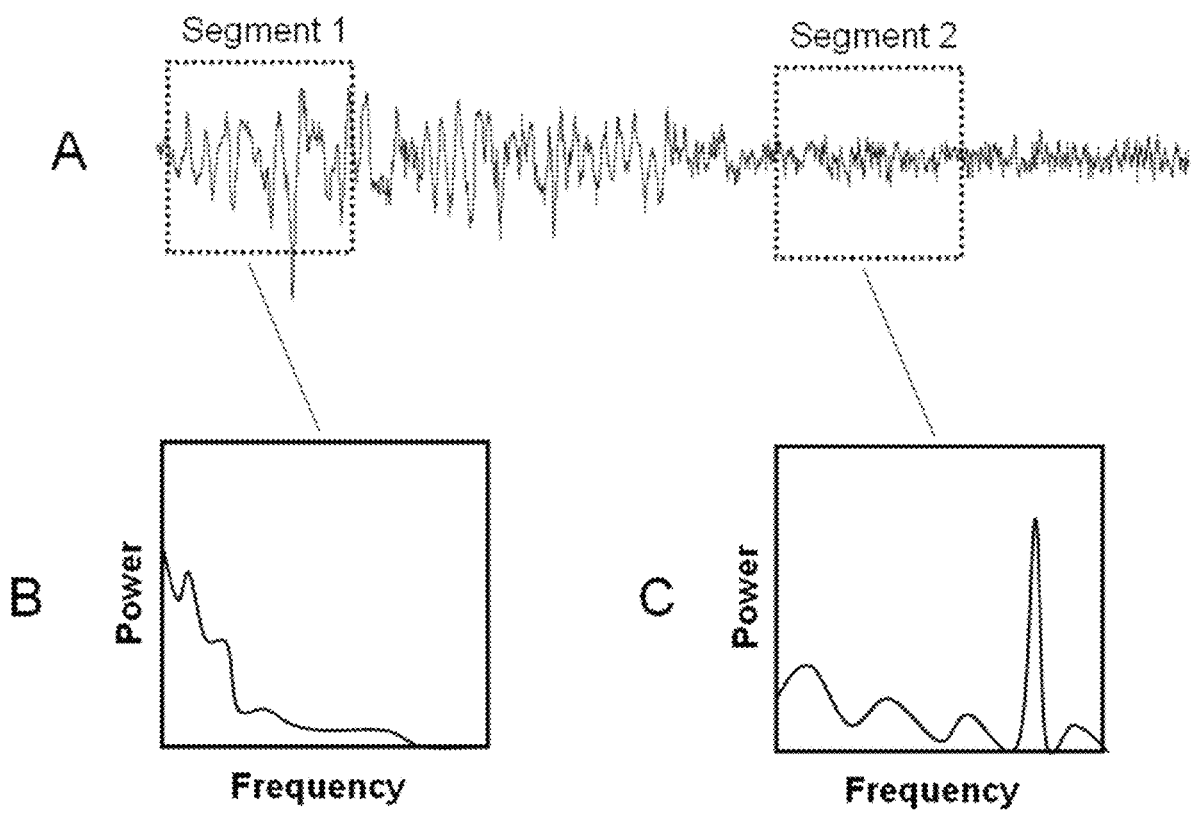
FIG. 7 includes illustrations of a seizure onset (panel A), and corresponding power spectral densities (panel B).

Another method that may be useful for determining if a low resolution waveform represents a clinically significant event involves assessing power changes within spectral bands. FIG. 7 includes illustrations of a seizure onset (panel A), and corresponding power spectral densities (panel B). FIG. 7 shows a seizure onset (panel A) that is characterized by an abrupt shift in spectral content. Segment 1 shows higher spectral power at the lower frequencies, as illustrated by the Power Spectral Density (PSD) plot in panel B. Segment 2 shows a power peak at higher frequencies as shown by the PSD plot in panel C. Because these spectral power shifts can be indicative of ictal onset, they may be useful for determining ECOGs of clinical interest. Because the ECOGs used in this analysis would be frequency limited by the under-sampling inherent in the lower resolution form, this method may be limited to waveforms where frequency content changes are evident at the lower sampled rate, or where sufficient higher frequency power content is aliased to lower frequencies.

Figure 8:
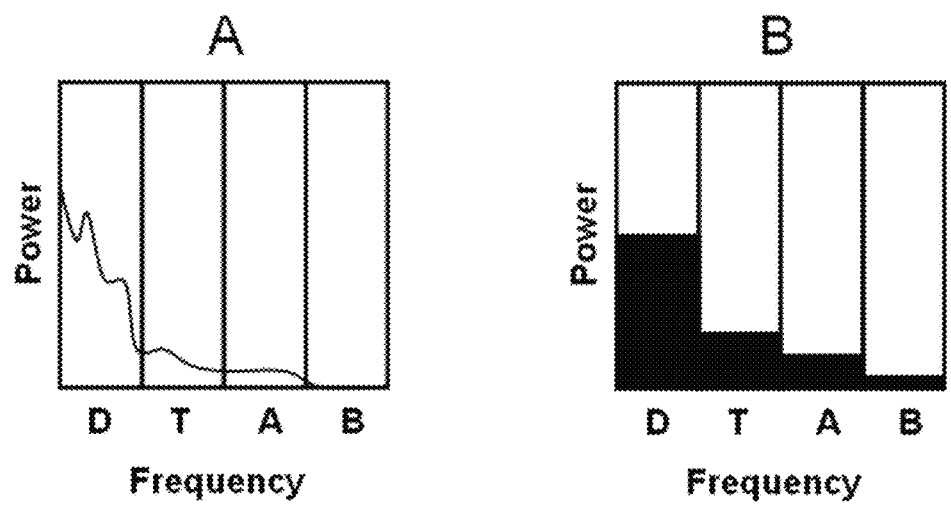
FIG. 8 includes illustrations of an ECOG segment transformed into a power spectral density.

FIG. 8 includes illustrations of an ECOG segment transformed into a power spectral density (PSD). The transformation may be made using standard techniques known to one of ordinary skill in the art. The power present within discrete frequency bands, such as those commonly used in clinical analysis (D=Delta, T=Theta, A=Alpha, B=Beta), are calculated by integrating the PSD within the discrete bandwidths to result in a small series of values representative of bandwidth power for each ECOG segment. The number of bandwidths would be typically 2 to 8.

Figure 9:
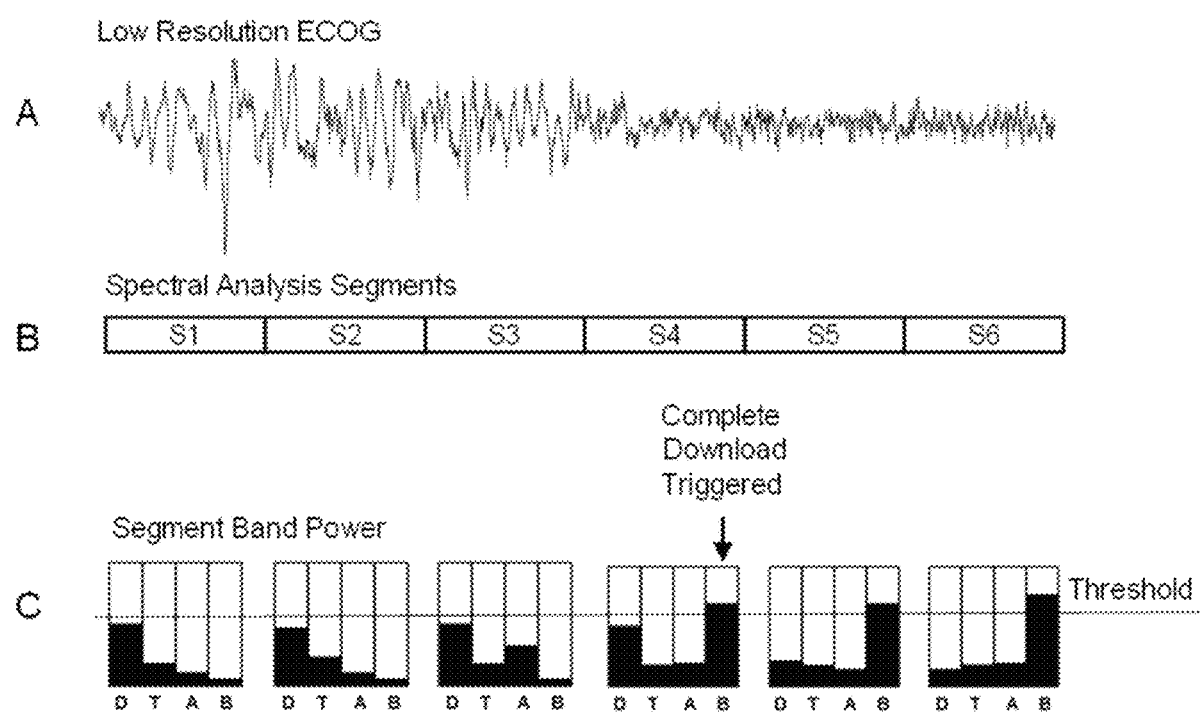
FIG. 9 further illustrates this embodiment.

FIG. 9 includes illustrations of an ECOG segment transformed into a number of segmented spectral analyses segments. Panel A shows the low resolution ECOG, which is broken up into a series of spectral analysis segments labeled S1 thru S6 in panel B. These spectral analysis segments are typically 1 to 30 seconds in duration. The spectral analysis segments may overlap in time in some embodiments to produce a smoothing effect if desired, but are shown without time overlap in FIG. 9. For each segment the PSD is calculated and the integrated band powers are determined (panel C). A low resolution waveform is deemed to represent a clinically significant event and full ECOG download is triggered when the band power of a frequency band satisfies a criterion corresponding to that particular frequency band. The criterion may be a threshold band power level and the criterion may be considered satisfied when the band power in exceeds the threshold. The criterion may be a threshold band power difference that is satisfied when the difference in the band power of a particular frequency between adjacent segments exceeds a given threshold. Furthermore, although the band power is shown as increasing in the example of FIG. 9, the threshold could be negative with power depletions being indicative of a clinically significant event.

Determining the band of interest may be performed in several ways. In one embodiment, a central user such as the programming physician could indicate the bandwidth to use based on detailed ECOG examination. In another embodiment the external apparatus could use certain operating points to collect ECOGS, which were then presented to the central user for comparison. For example, the external apparatus could collect a series of ECOGs with the greatest power change in each of the several bandwidths, and the user could indicate which bandwidth best triggered most meaningful ECOG download. In another embodiment, the power changes present in the different bandwidths could be compared to seizure diary data collected from the patient. These data could be collected using an on-line entry system, or by a device feature such as a magnetic field sensor that could trigger when the patient placed a magnet on the implanted device.

Once the bandwidth of interest is determined, the criterion for determining if a low resolution waveform represents a clinically significant event may be determined in several ways. In one configuration, the running average of several summation spectral analysis segments at the beginning of each ECOG may be used as a baseline. Abrupt changes within an ECOG, relative to the baseline, would be indicative of a low resolution waveform that represents a clinically significant event would trigger full ECOG download. An abrupt change in spectral power may correspond to a value or percentage above baseline. Use of a running average is beneficial in that it allows for biocalibration of the threshold based on inherent background power levels which vary based on neural state (asleep, drowsy, awake, alert, etc). In this manner the band power or band power difference threshold for an individual ECOG could be set as a multiple (100%, 200%, etc.) of the baseline band power or baseline band power differences observed at the beginning of that ECOG.

In another configuration, the external apparatus may be configured to always fully retrieve a fixed number of ECOGs (1, 2, etc.). In this case, the external apparatus derives a power metric, e.g., band power or band power difference, for each available low-resolution ECOG that is being considered for retrieval, and selects for full download, a number of low resolution ECOGs corresponding to the fixed number based on the respective metrics. For example, if the external apparatus is configured to retrieve 3 full resolution ECOGs per interrogation session, the ECOGs with the three highest band powers or band power differences are selected.

The band power threshold could also be determined based on measured changes determined during prior ECOG retrieval sessions. For example, the external apparatus may have an evolving threshold that triggers full download for ECOGs that exhibit band powers or band power difference that exceed a certain percentage of observations for all prior sessions. In this embodiment, the external apparatus tracks all ECOG band power or band power difference values over all retrieval sessions, and then sets the threshold to a percentage of the prior observations (80%, 90%, etc.). Metrics, e.g., band power or band power difference, are derived for new ECOGs and compared to the threshold. If the metric of the new ECOG exceeds the corresponding metric of the threshold percentage of the prior ECOGs, the new ECOG is determined to be a clinically significant event. For example, if the threshold percentage is 80% and the metric of the new ECOG is greater than the same metric of 80% of the prior ECOGs, the new ECOG is clinically significant, and a full download of the new ECOG is triggered. As new ECOGs are presented, the external apparatus adjusts the threshold. In this manner the ECOGs with the most powerful segments or segment differences would always be fully retrieved, which presumably would have the highest clinical significance.

The selection of ECOG waveforms for full resolution upload may be based on template matching. In this configuration, a low resolution waveform is evaluated and categorized based on how well it matches any number of pre-specified template waveforms. A metric of how well a low resolution waveform fits a template may be scored based on a cross-correlation calculation of the low resolution waveform and the template. If the metric satisfies a criterion, the physiological signal corresponding to the low resolution version may be determined to represent a clinically significant event.

The selection of ECOG waveforms for full resolution upload is optimized to exhibit diversity. In this configuration, the intent is to present the physician with fully uploaded ECOG records that represent the variety of ECOG types recorded from a given patient to contribute to the physician's understanding of the patient's condition. This reduces the likelihood that the physician would be presented with an artificially homogenous set of ECOG records based on the selection criteria used for full resolution uploads. In this embodiment priority for full resolution upload is granted to any ECOG record having a low resolution version that exhibits different characteristics than the majority of ECOG records recently selected for full resolution upload. For example, if the most recent 10 ECOG records that were selected for full resolution upload were so selected based on a sudden increase in signal power as described above, then priority may be granted to the next ECOG record that displays a frequency shift or some other characteristic that is not represented in the set of recently fully uploaded ECOG records.

An implantable medical device may be configured to transmit compressed signals or to transmit full resolution signals. The decision to transmit compressed waveforms could be based on a programmed setting in the implanted device, or it could be based on a setting in the data repository that is communicated to a home data monitor. In the later case the physician would have the option to remotely select compressed or non-compressed waveforms based on patient needs without altering the implanted device software or programming.

Figure 10:
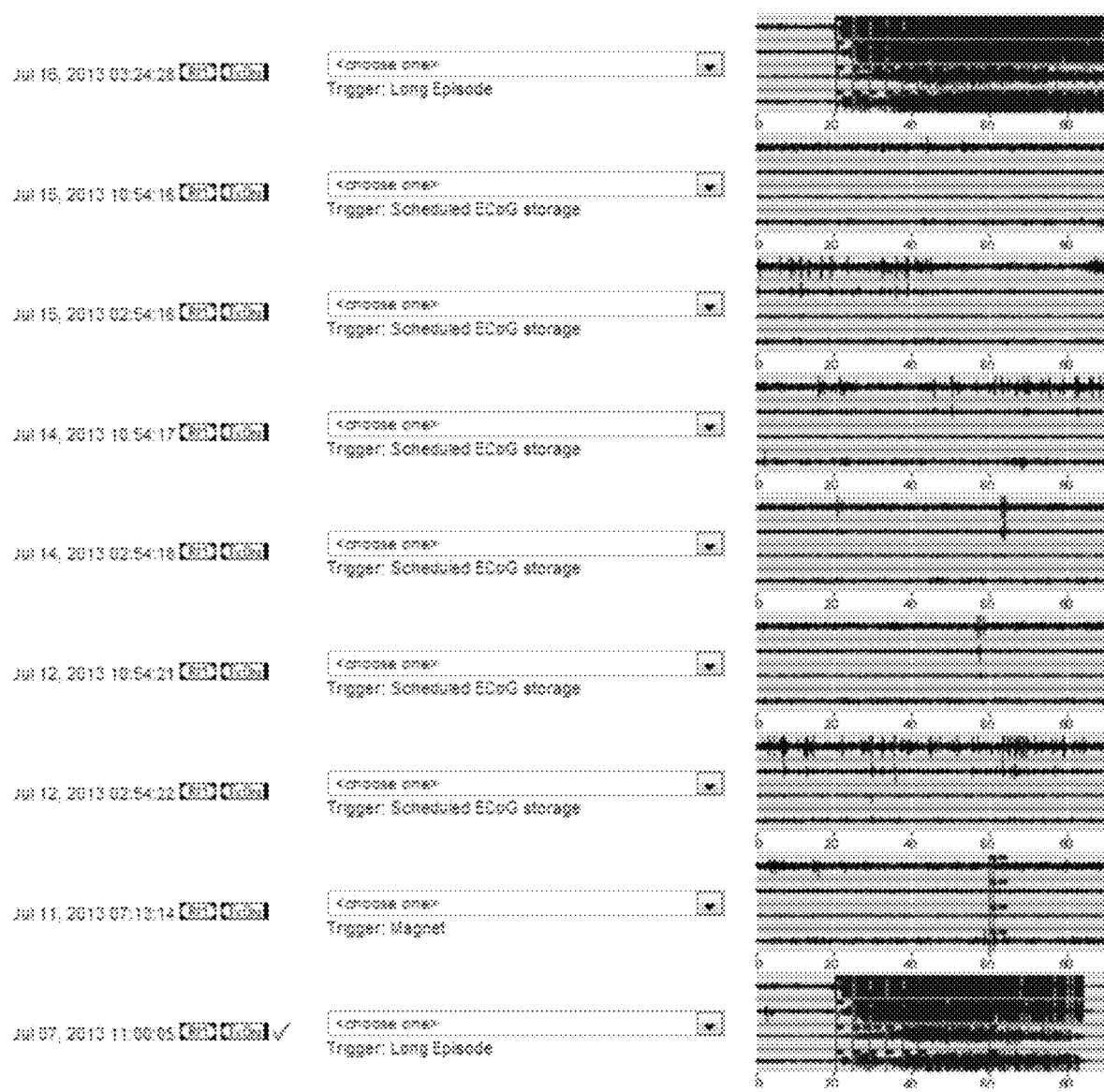
FIG. 10 includes illustrations of several ECOGs from an epilepsy patient are displayed in low resolution thumbnail mode.

FIG. 10 includes illustrations of several ECOGs from an epilepsy patient displayed in low resolution thumbnail mode. This figure shows thumbnail resolution images of ECOGs that convey events that are seizures. It would be clear to a physician specializing in the treatment of epilepsy that the first and last ECOGs are seizures. Furthermore, based on observation the physician may determine that compressed waveforms are adequate to care for this patient and may elect to reduce energy consumption by compressing all waveform data for transmission to enhance the battery life of the implanted device. A decision to implement compression of physiological waveform may be made if the programmed settings for the implantable device have been stable for a long period of time and the user has determined that compressed waveform data are adequate for diagnostic purposes and the battery longevity improvement that results from reduced telemetry energy use from such compression is beneficial for the patient.

Figure 11:
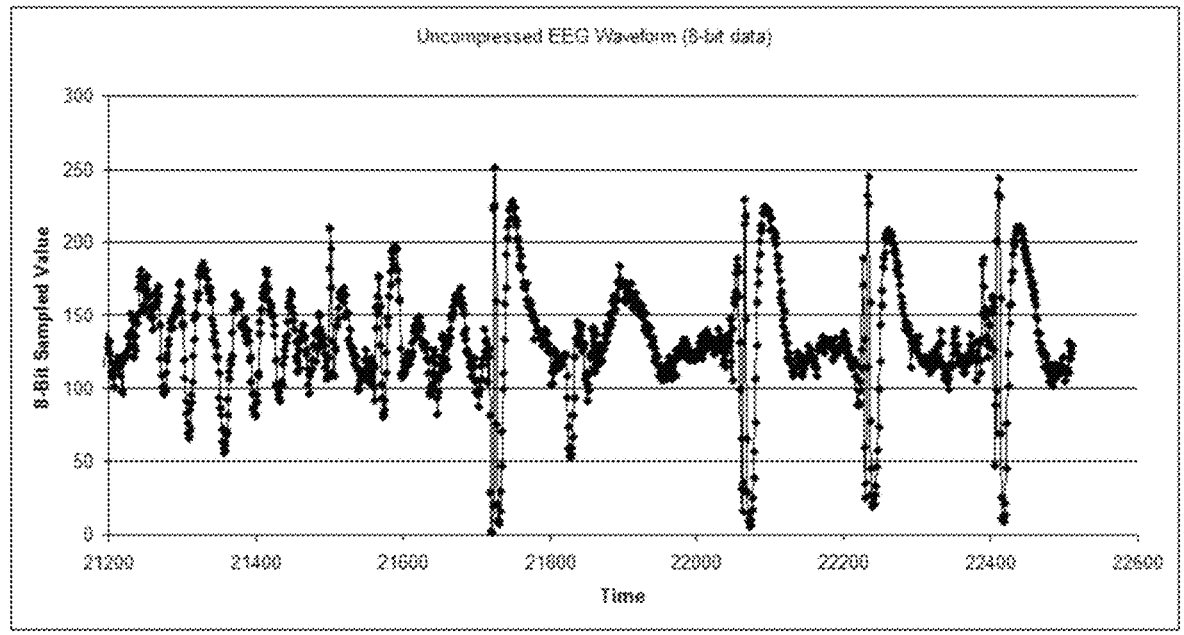
FIG. 11 is an illustration of an uncompressed, full resolution ECOG waveform.
Figure 12:
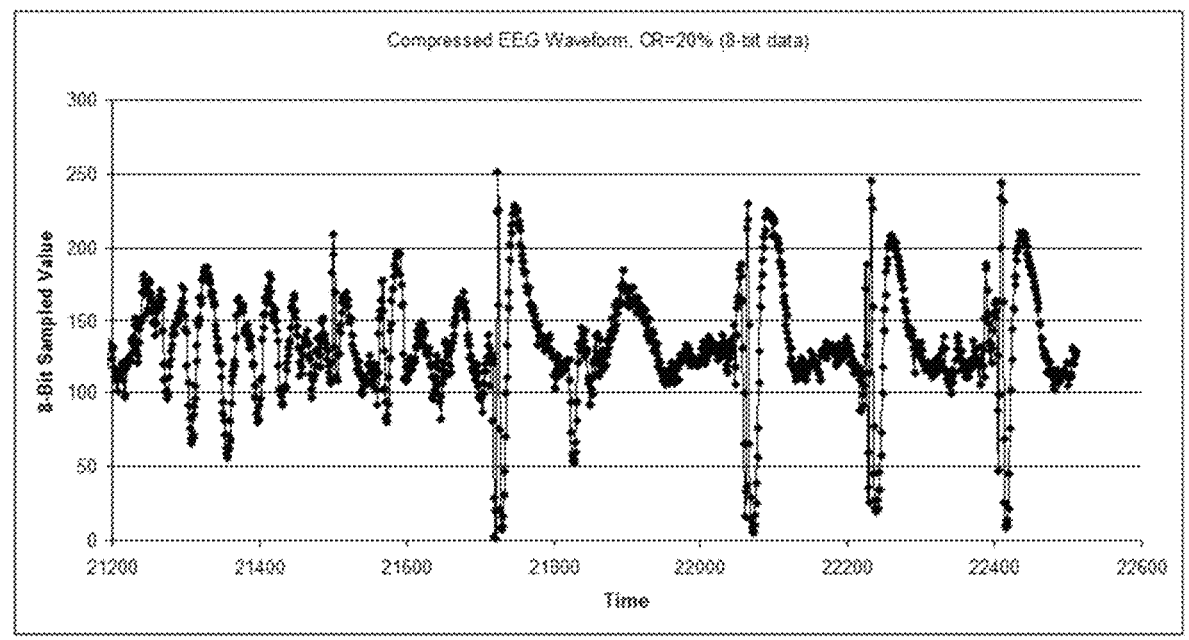
FIG. 12 is an illustration of a low resolution version of the waveform from FIG. 11.

FIG. 11 is an illustration of an uncompressed, full resolution ECOG waveform. FIG. 12 is an illustration of a low resolution version of the waveform from FIG. 11. FIG. 12 shows that a good representation of an ECOG waveform can be viewed with only 1/5.26 (about 20%) of the data used to represent the full waveform. Less than 20% of the data from FIG. 11 was used to generate this plot. The compression ratio (CR) shown here is 5.26.

Figures 13, 14:
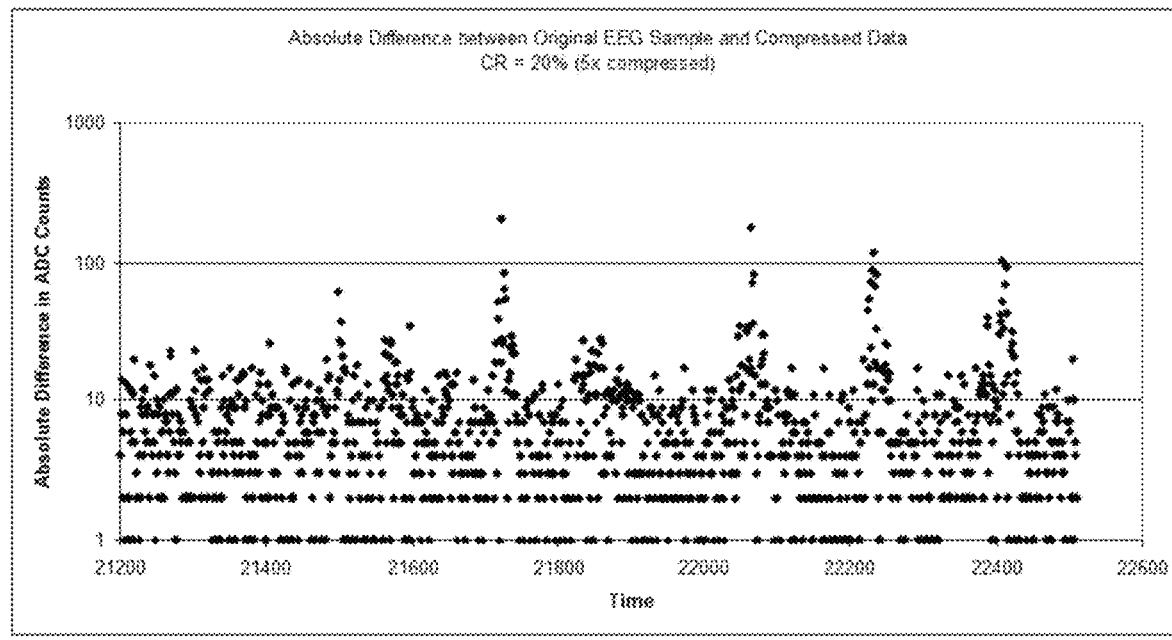
FIG. 13 is an illustration of a plot of the absolute difference between the data presented in FIG. 11 and FIG. 12.
FIG. 14 is a histogram of the data presented in FIG. 13.

FIG. 13 is an illustration of a plot of the absolute difference between the data presented in FIG. 11 and FIG. 12. The plot of FIG. 13 allows for a visualization of the difference between the low resolution and the full resolution data is to actually plot the difference. FIG. 13 shows that more than 50% of the points are within 5 counts of the full resolution waveform. More than 75% of the samples are within 10 counts. The difference between the data from FIG. 11 and FIG. 12 can also be expressed as a histogram of the data presented in FIG. 13. This data is presented in FIG. 14.

Figure 15:
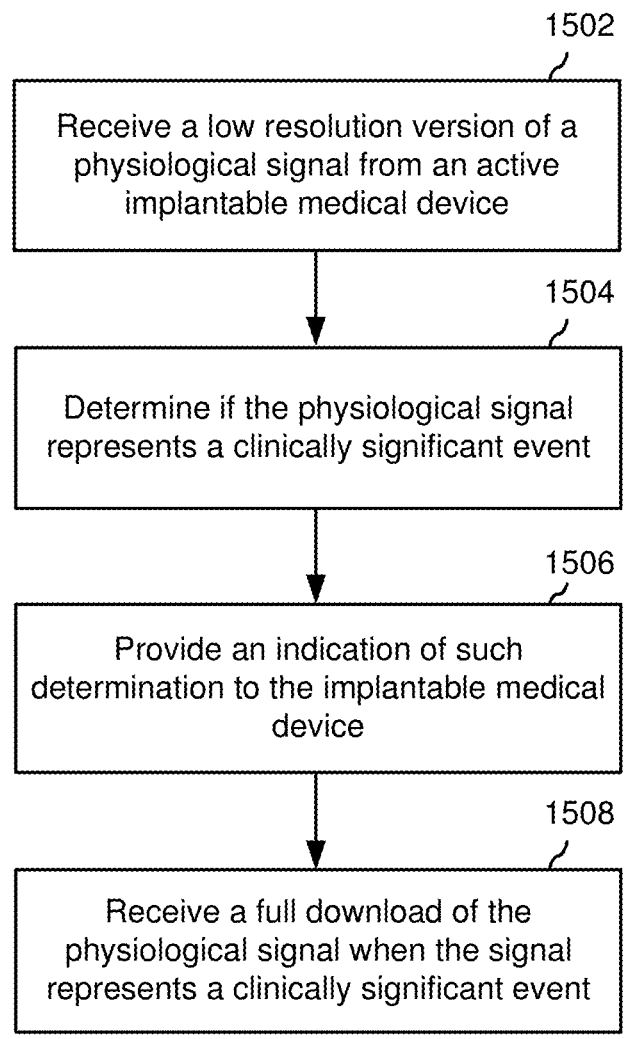
FIG. 15 is a flow chart of a method of retrieving data from an implantable medical device.

FIG. 15 is a flow chart of a method of retrieving data from an implantable medical device. The method may be performed by an external apparatus, such as a programmer or remote home monitoring device configured to communicate with the implantable medical device. At step 1502, the external apparatus receives a low resolution version of a physiological signal from an active implantable medical device. The low resolution signal may be a portion of a compressed version of a physiological signal, e.g., ECOG, sensed by the implantable medical device. The signal may be compressed using a progressive encoding technique, such as JPEG. The signal may be received by the external apparatus by wireless telemetry, such as previously described with reference to FIG. 4.

At step 1504, the external apparatus determines if the physiological signal represents a clinically significant event. The external apparatus may process the signal to detect for a change in power in the low resolution signal that is indicative of a clinically significant event. For example, the external apparatus may derive a power metric for the low resolution signal, and compare the power metric to a criterion, e.g., a threshold, that when met serves as an indication of a clinically significant event. In one implementation, the power metric may be a segmented power metric for a time segment of the low resolution signal. In this case, the criterion is met when the segmented power metric exceeds a power level threshold. In another implementation, the power metric may be a difference between adjacent segmented power metrics, where each segmented power metric corresponding to a power metric in a respective time segment of the low resolution signal. In this case, the criterion is met when the difference exceeds a power change threshold.

In another implementation, the power metric may be a frequency band power metric for a time segment of the low resolution signal. In this case, the criterion is met when the frequency band power metric exceeds its corresponding power level threshold. In yet another implementation, the power metric may be a difference between corresponding frequency band power metrics of adjacent time segments of the low resolution signal. In this case, the criterion is met when the differences exceeds a power change threshold for the frequency band.

At step 1506, the external apparatus provides an indication of such determination to the implantable medical device. For example, the external apparatus may transmit a trigger signal to the implantable device requesting a full download of the compressed file corresponding to the low resolution version. The trigger signal may be sent over wireless telemetry.

Figure 16:
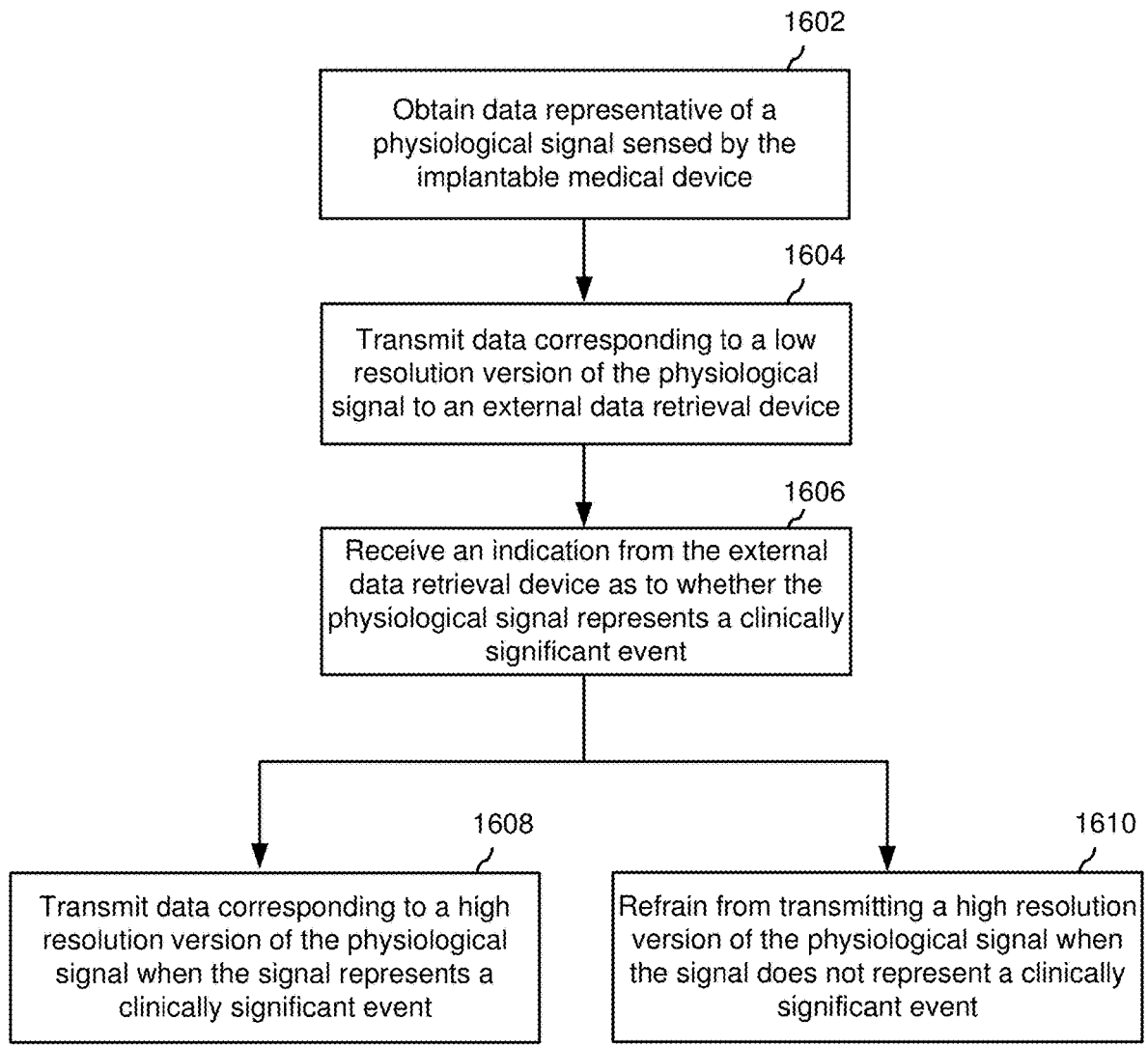
FIG. 16 is a flow chart of a method of data transmission by an implantable medical device.

FIG. 16 is a flow chart of a method of data transmission. The method may be performed by an active implantable medical device configured to communicate with an external apparatus. At step 1602, the device obtains data representative of a physiological signal sensed by the implantable medical device. The device may sense physiological activity through one or more electrodes and record data representative of the activity. For example, the device may record ECOG waveforms in a compressed format, such as JPEG.

At step 1604, the device transmits data corresponding to a low resolution version of the physiological signal to an external data retrieval device. The transmission may be in response to an interrogation by the external apparatus. The low resolution version may correspond to a portion of the full recording of the physiological signal sufficient to allow the external apparatus to determine whether the physiological signal represents a clinically significant event.

At step 1606, the device receives an indication from the external data retrieval device as to whether the physiological signal represents a clinically significant event. For example, the external apparatus may transmit a trigger signal to the implantable device requesting a full download of the compressed file corresponding to the low resolution version. The trigger signal may be received by the device over wireless telemetry.

At step 1608, the device transmits data corresponding to a high resolution version of the physiological signal when the signal represents a clinically significant event. At step 1610, the device refrains from transmitting a high resolution version of the physiological signal when the signal does not represent a clinically significant event.

Figure 17:
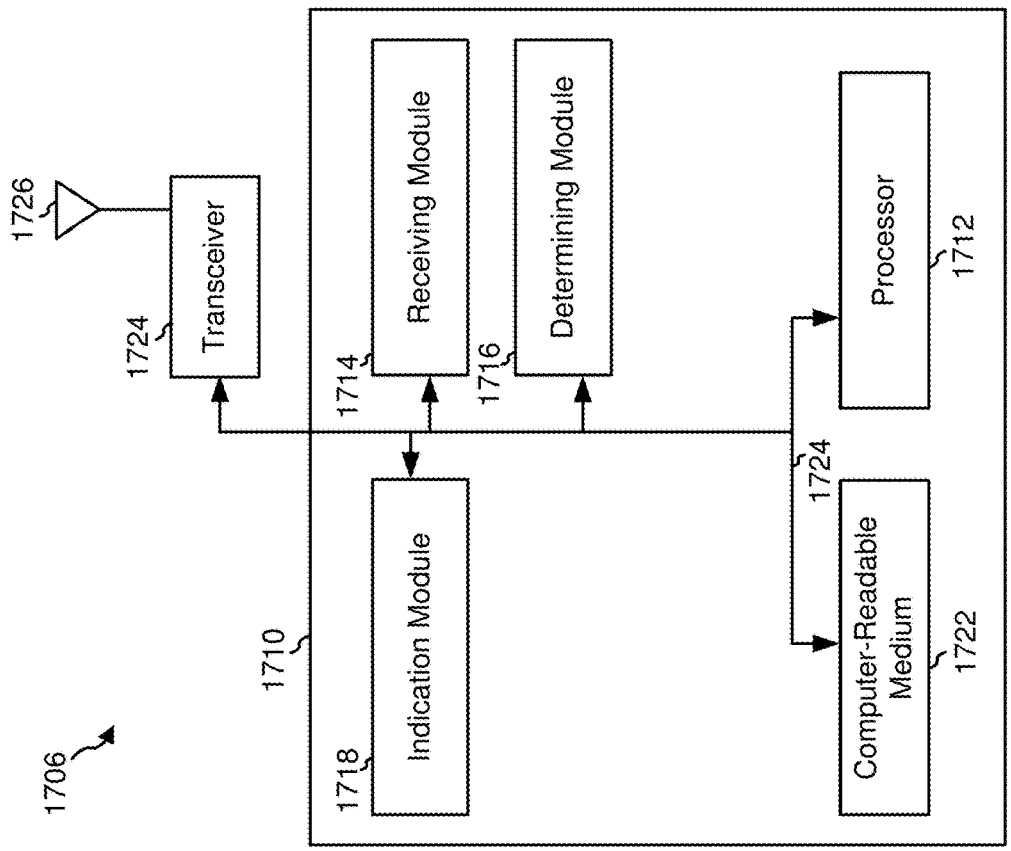
FIG. 17 is a hardware implementation of a data retrieval apparatus.

FIG. 17 is a diagram illustrating an example of a hardware implementation for a data retrieval apparatus 1706 that implements the method of FIG. 15. The apparatus 1706 employs a processing system 1710. The processing system 1710 may be implemented with a bus architecture, represented generally by the bus 1724. The bus 1724 may include any number of interconnecting buses and bridges depending on the specific application of the processing system 1710 and the overall design constraints. The bus 1724 links together various circuits including one or more processors and/or hardware modules, represented by the processor 1712, a receiving module 1714, a determining module 1716, an indication module 1718, and a computer-readable medium 1722. The bus 1724 may also link various other circuits such as timing sources, peripherals, voltage regulators, and power management circuits, which are well known in the art, and therefore, will not be described any further.

The receiving module 1714 is configured to receive a low resolution version of a physiological signal from an active implantable medical device. The determining module 1716 is configured to determine if the physiological signal represents a clinically significant event. The indication module 1718 is configured to provide an indication of such determination to the implantable medical device.

The modules 1714, 1716 and 1718 may be software modules running in the processor 1712, resident/stored in the computer readable medium 1722, one or more hardware modules coupled to the processor 1712, or some combination thereof. The processing system 1710 may be coupled to a transceiver 1724. The transceiver 1724 is coupled to one or more antennas 1726. The transceiver 1724 provides a means for communicating with various other apparatus over a transmission medium, including for example an implantable medical device. The transceiver 1724 receives a signal from the one or more antennas 1726, extracts information from the received signal, and provides the extracted information to the processing system 1710. In addition, the transceiver 1724 receives information from the processing system 1710 and based on the received information, generates a signal to be applied to the one or more antennas 1726.

The processing system 1710 includes a processor 1712 coupled to a computer-readable medium 1722. The processor 1712 is responsible for general processing, including the execution of software stored on the computer-readable medium 1722. The software, when executed by the processor 1712, causes the processing system 1710 to perform the various functions described supra for any particular module. The computer-readable medium 1722 may also be used for storing data that is manipulated by the processor 1712 when executing software.

Figure 18:
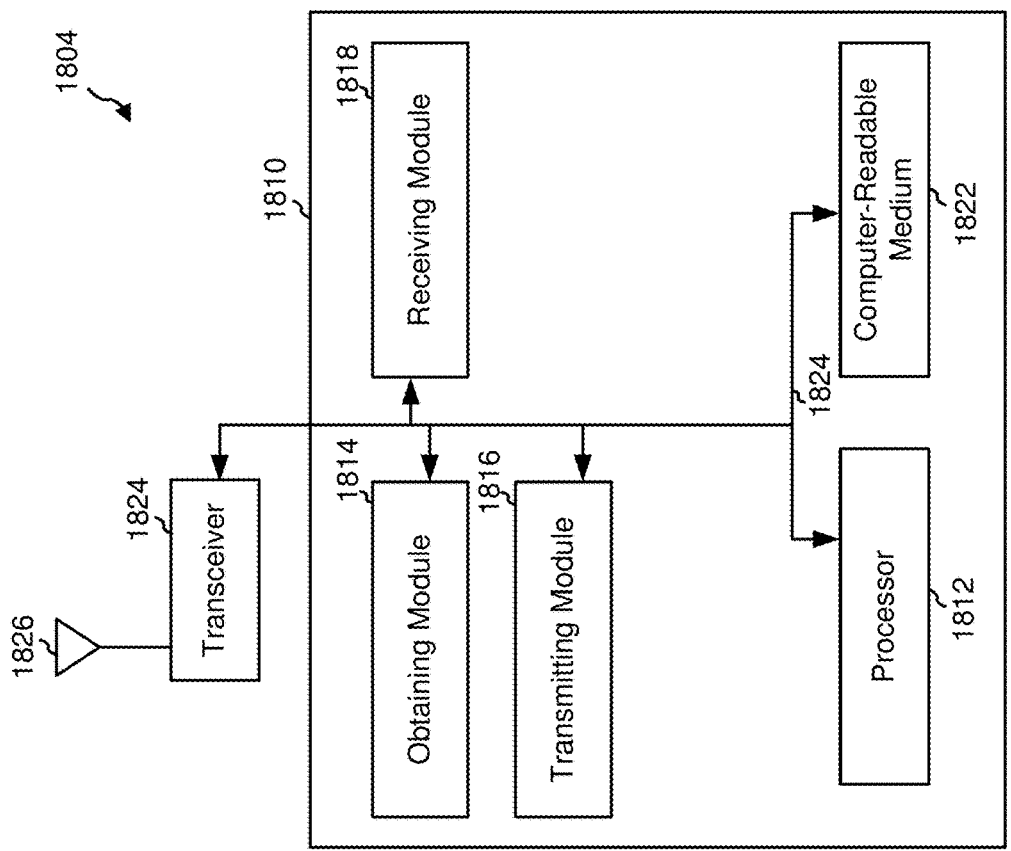
FIG. 18 is a diagram of an exemplary hardware implementation of an implantable medical device.

FIG. 18 is a diagram illustrating an example of a hardware implementation for an active implantable medical device 1804 that implements the method of FIG. 16. The device employs a processing system 1810. The processing system 1810 may be implemented with a bus architecture, represented generally by the bus 1824. The bus 1824 may include any number of interconnecting buses and bridges depending on the specific application of the processing system 1810 and the overall design constraints. The bus 1824 links together various circuits including one or more processors and/or hardware modules, represented by the processor 1812, a obtaining module 1814, a transmitting module 1816, a receiving module 1818, and a computer-readable medium 1822. The bus 1824 may also link various other circuits such as timing sources, peripherals, voltage regulators, and power management circuits, which are well known in the art, and therefore, will not be described any further.

The obtaining module 1814 is configured to obtain data representative of a physiological signal sensed by the implantable medical device. The transmitting module 1816 is configured to transmit data corresponding to a low resolution version of the physiological signal to an external data retrieval device, and to subsequently transmit data corresponding to a high resolution version of the physiological signal when the signal represents a clinically significant event. The transmitting module is further configured to refrain from transmitting a high resolution version of the physiological signal when the signal does not represent a clinically significant event. The receiving module 1818 is configured to receive an indication from the external data retrieval device as to whether the physiological signal represents a clinically significant event.

The modules 1814, 1816 and 1818 may be software modules running in the processor 1812, resident/stored in the computer readable medium 1822, one or more hardware modules coupled to the processor 1812, or some combination thereof. The processing system 1810 may be coupled to a transceiver 1824. The transceiver 1824 is coupled to one or more antennas 1826. The transceiver 1824 provides a means for communicating with various other apparatus over a transmission medium, including for example an external apparatus. The transceiver 1824 receives a signal from the one or more antennas 1826, extracts information from the received signal, and provides the extracted information to the processing system 1810. In addition, the transceiver 1824 receives information from the processing system 1810 and based on the received information, generates a signal to be applied to the one or more antennas 1826.

The processing system 1810 includes a processor 1812 coupled to a computer-readable medium 1822. The processor 1812 is responsible for general processing, including the execution of software stored on the computer-readable medium 1822. The software, when executed by the processor 1812, causes the processing system 1810 to perform the various functions described supra for any particular module.

The computer-readable medium 1822 may also be used for storing data that is manipulated by the processor 1812 when executing software.

This invention extends the usable service life of implantable devices by reducing the amount of data that must be retrieved from the implant over the high power telemetry link.

Methods and apparatuses disclosed herein allow external equipment to determine which physiological signals, e.g., ECOG waveform, are of interest. The external equipment has much greater computing power and sophistication than the implantable device. Allowing the external equipment to determine which waveforms are of interest allows more complex decision making criteria to be used. Any one of several criteria described above may be used to by the external equipment to determine if a particular waveform is valuable enough to trigger a full download of the signal from the implantable device.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of retrieving an electrographic waveform stored in a memory of an active implantable medical device as a progressive encoded file, the method comprising:
    initiating, with the active implantable medical device, an uploading of an entirety of the progressive encoded file;
    receiving, at an external data retrieval apparatus, a portion of the entirety of the progressive encoded file;
    determining, at the external data retrieval apparatus, if a low-resolution version of the electrographic waveform derived from the portion of the entirety of the progressive encoded file represents a clinically significant event;
    responsive to a determination that the low-resolution version of the electrographic waveform does not represent a clinically significant event, discontinuing the uploading of the entirety of the progressive encoded file; and
    responsive to a determination that the low-resolution version of the electrographic waveform represents a clinically significant event, continuing the uploading of the entirety of the progressive encoded file.

2. The method of claim 1, wherein discontinuing the uploading of the entirety of the progressive encoded file comprises providing, to the active implantable medical device, an indication of the determination that the low-resolution version of the electrographic waveform does not represent a clinically significant event.

3. The method of claim 1, wherein continuing the uploading of the entirety of the progressive encoded file comprises providing, to the active implantable medical device, an indication of the determination that the low-resolution version of the electrographic waveform represents a clinically significant event.

4. The method of claim 1, wherein determining if a low resolution version of the electrographic waveform derived from the portion of the entirety of the progressive encoded file represents a clinically significant event comprises:
    partitioning the low resolution version of the electrographic waveform into a plurality of time segments;
    deriving a power metric for each of the plurality of time segments;
    deriving a criterion, which when met serves as an indication of a clinically significant event, based on the power metrics of one or more time segments that include a baseline portion of the low resolution version of the electrographic waveform;
    obtaining a metric for comparison with the criterion, the metric based on the power metrics of one or more time segments subsequent to the baseline portion of the low resolution version of the electrographic waveform; and
    comparing the metric to the criterion.

5. The method of claim 4, wherein the power metric is a measure of power obtained from a time domain version of the low resolution version of the electrographic waveform.

6. The method of claim 4, wherein the power metric is a measure of power spectral density obtained from a frequency domain version of the low resolution version of the electrographic waveform.

7. The method of claim 6, wherein the measure of power spectral density is for a particular frequency band.

8. The method of claim 1, further comprising:
    responsive to discontinuing the uploading of the entirety of the progressive encoded file, storing the low-resolution version of the electrographic waveform.

9. The method of claim 1, wherein the entirety of the progressive encoded file represents a full resolution version of the electrographic waveform.

10. An external data retrieval apparatus configured to retrieve an electrographic waveform stored in a memory of an active implantable medical device as a progressive encoded file, the apparatus comprising:
    a transceiver;
    a memory; and
    at least one processor coupled to the transceiver and the memory and configured to:
        initiate an uploading of an entirety of the progressive encoded file with the active implantable medical device;
        receive a portion of the entirety of the progressive encoded file from the active implantable medical device;
        determine if a low-resolution version of the electrographic waveform derived from the portion of the entirety of the progressive encoded file represents a clinically significant event;
        discontinue the uploading of the entirety of the progressive encoded file in response to a determination that the low-resolution version of the electrographic waveform does not represent a clinically significant event; and
        continue the uploading of the entirety of the progressive encoded file in response to a determination that the low-resolution version of the electrographic waveform represents a clinically significant event.

11. The apparatus of claim 10, wherein the at least one processor discontinues the uploading of the entirety of the progressive encoded file by being further configured to:

provide, to the active implantable medical device, an indication of the determination that the low-resolution version of the electrographic waveform does not represent a clinically significant event.

12. The apparatus of claim 10, wherein the at least one processor continues the uploading of the entirety of the progressive encoded file by being further configured to:

provide, to the active implantable medical device, an indication of the determination that the low-resolution version of the electrographic waveform represents a clinically significant event.

13. The apparatus of claim 10, wherein the at least one processor determines if a low resolution version of the electrographic waveform derived from the portion of the entirety of the progressive encoded file represents a clinically significant event by being further configured to:

partition the low resolution version of the electrographic waveform into a plurality of time segments;

derive a power metric for each of the plurality of time segments;

derive a criterion, which when met serves as an indication of a clinically significant event, based on the power metrics of one or more time segments that include a baseline portion of the low resolution version of the electrographic waveform;

obtain a metric for comparison with the criterion, the metric based on the power metrics of one or more time segments subsequent to the baseline portion of the low resolution version of the electrographic waveform; and compare the metric to the criterion.

14. The apparatus of claim 13, wherein the power metric is a measure of power obtained from a time domain version of the low resolution version of the electrographic waveform.

15. The apparatus of claim 13, wherein the power metric is a measure of power spectral density obtained from a frequency domain version of the low resolution version of the electrographic waveform.

16. The apparatus of claim 15, wherein the measure of power spectral density is for a particular frequency band.

17. The apparatus of claim 10, wherein the at least one processor is further configured to:

responsive to discontinuing the uploading of the entirety of the progressive encoded file, store the low-resolution version of the electrographic waveform.

18. The apparatus of claim 10, wherein the entirety of the progressive encoded file represents a full resolution version of the electrographic waveform.

* * * * *